United States Patent [19]

Baldwin et al.

[11] 4,075,632
[45] Feb. 21, 1978

[54] INTERROGATION, AND DETECTION SYSTEM

[75] Inventors: Howard A. Baldwin; Steven W. Depp; Alfred R. Koelle; Robert W. Freyman, all of Los Alamos, N. Mex.

[73] Assignee: The United States of America as represented by the United States Department of Energy, Washington, D.C.

[21] Appl. No.: 689,708

[22] Filed: May 24, 1976

Related U.S. Application Data

[63] Continuation of Ser. No. 501,020, Aug. 27, 1974, abandoned.

[51] Int. Cl.$^2$ .......................... G01S 9/56; H04B 1/59
[52] U.S. Cl. .................................. 343/6.8 R; 325/113
[58] Field of Search ...................... 343/6.8 R, 6.8 LC; 325/8, 113, 140

[56] References Cited

U.S. PATENT DOCUMENTS

| 2,927,321 | 3/1960 | Harris | 343/6.8 R X |
| 3,070,773 | 12/1962 | Woolston et al. | 325/113 X |
| 3,253,588 | 5/1966 | Vuilleumier et al. | 325/113 X |
| 3,319,167 | 5/1967 | Bray et al. | 325/113 X |
| 3,453,546 | 7/1969 | Fryer | 325/113 X |
| 3,460,139 | 8/1969 | Rittenbach | 343/6.5 R X |
| 3,475,742 | 10/1969 | Whitney et al. | 325/113 X |

Primary Examiner—Malcolm F. Hubler
Attorney, Agent, or Firm—Dean E. Carlson; Jerome B. Rockwood

[57] ABSTRACT

The specification relates to a telemetering apparatus comprising a generator which generates at least a single frequency rf signal, a transponder for receiving that signal and for amplitude modulating it in accordance with information selected for transmission, an antenna on the transponder for reflecting the amplitude modulated signal, and a receiver which is preferably located at the generator. The receiver processes the signal to determine the information carried thereby.

10 Claims, 8 Drawing Figures

Modulation by loading rectifier

Fig. 4

Modulation by pin diode

INTERROGATION, AND DETECTION SYSTEM

The invention described herein was made in the course of, or under, a contract with the U.S. ATOMIC ENERGY COMMISSION.

This is a continuation of application Ser. No. 501,020, filed Aug. 27, 1974, now abandoned.

FIELD OF THE INVENTION

The invention relates to telemetering and in particular to a system for amplitude modulating a first signal in accordance with selected information and for reflecting the amplitude modulating signal to a receiver for processing the modulated signal to determine the information carried thereby.

BACKGROUND OF THE INVENTION

Although the system of the invention has many applications, including, but not limited to motor vehicle identification, railroad car identification, inventory control, security systems, locating and tracking vehicles, monitoring from inaccessible locations, downed aircraft location, battlefield monitoring, and environmental monitoring, the preferred embodiment was developed for biomedical monitoring and in particular for identifying the health of selected animals. It will be appreciated by those skilled in the art that many methods of identifying animals are practiced by those in the livestock industry. However, none of these prior art methods are universally effective or utilized because of various shortcomings in each of such systems. Exemplary of those shortcomings are loss of the identification carried by the animal, poor visibility of the animal, and human errors in reading or transcribing.

There has been an existing need in the agricultural industry to identify particular animals and to determine, for example, the temperature of the animal as an indication of its health. It would be preferable that an animal monitoring system be amenable to automation and compatible with computer data processing methods so that much information on many animals can be more easily and errorlessly processed than has been possible with prior art systems. The system of the invention can be used to facilitate detailed records on such things as pedigree, food intake, fertility, preventative medical care, resistance to a disease, response to treatment, costs, sales, show performance and livestock movement. For food animals the invention can provide information from which one can compute conversion efficiency and relate management practices to carcass properties. The system of the invention has use in herd improvement for processing and determining relevant information from more factors than it is presently economical to consider.

In addition, the remote monitoring afforded by practicing the invention eliminates excess animal handling by humans and the attendant risk to personnel and animal. The system also eliminates the stress-induced temperature increase frequently associated with handling animals.

SUMMARY OF THE INVENTION

In accordance with the invention, there is provided a telemetering apparatus and method comprising a radio frequency or other frequency signal generator, a transmitter for transmitting a time variant signal comprising at least a selected single frequency, a transponder spaced from the transmitter for receiving and for amplitude modulating the signal in accordance with selected information, and a reflecting antenna which returns the amplitude modulated signal to a receiver preferably integral with the generator and transmitter. The receiver processes the modulated return signal to determine the selected information carried thereby. In a preferred embodiment of the invention, the transponder is passive and in an alternative embodiment is active. Both analog and digital information can be transmitted using the system of the invention.

The preferred embodiment of this telemetry system includes means for avoiding the dependence of the phase of the received signal, relative to that of the carrier, upon the physical distance between the interrogator antennas and the transponder antenna. If no such means were used, then the signals would be in quadrature phase relationship every quarter wavelength in spacing between the antennas and there would be zero output from the mixer at the modulating frequency.

One object of the invention is to provide an apparatus and method for animal monitoring.

Another object of the invention is to provide new telemetry capability.

One advantage of the instant invention is that the preferred embodiment thereof utilizes a transponder which eliminates the need for a separate energy source at the transponder.

Another advantage of the instant invention is that in accordance therewith, multiple digit information can be transmitted.

Another advantage of the instant invention is that there is no interference between the transmitted and received signal even though the transmission is continuous.

Still other objects and advantages of the present invention will be apparent to those skilled in the art from the following description, with reference to the appended drawings, wherein like numbers denote like parts and wherein.

DETAILED DESCRIPTION OF A PREFERRED EMBODIMENT OF THE INVENTION

Figure 1:
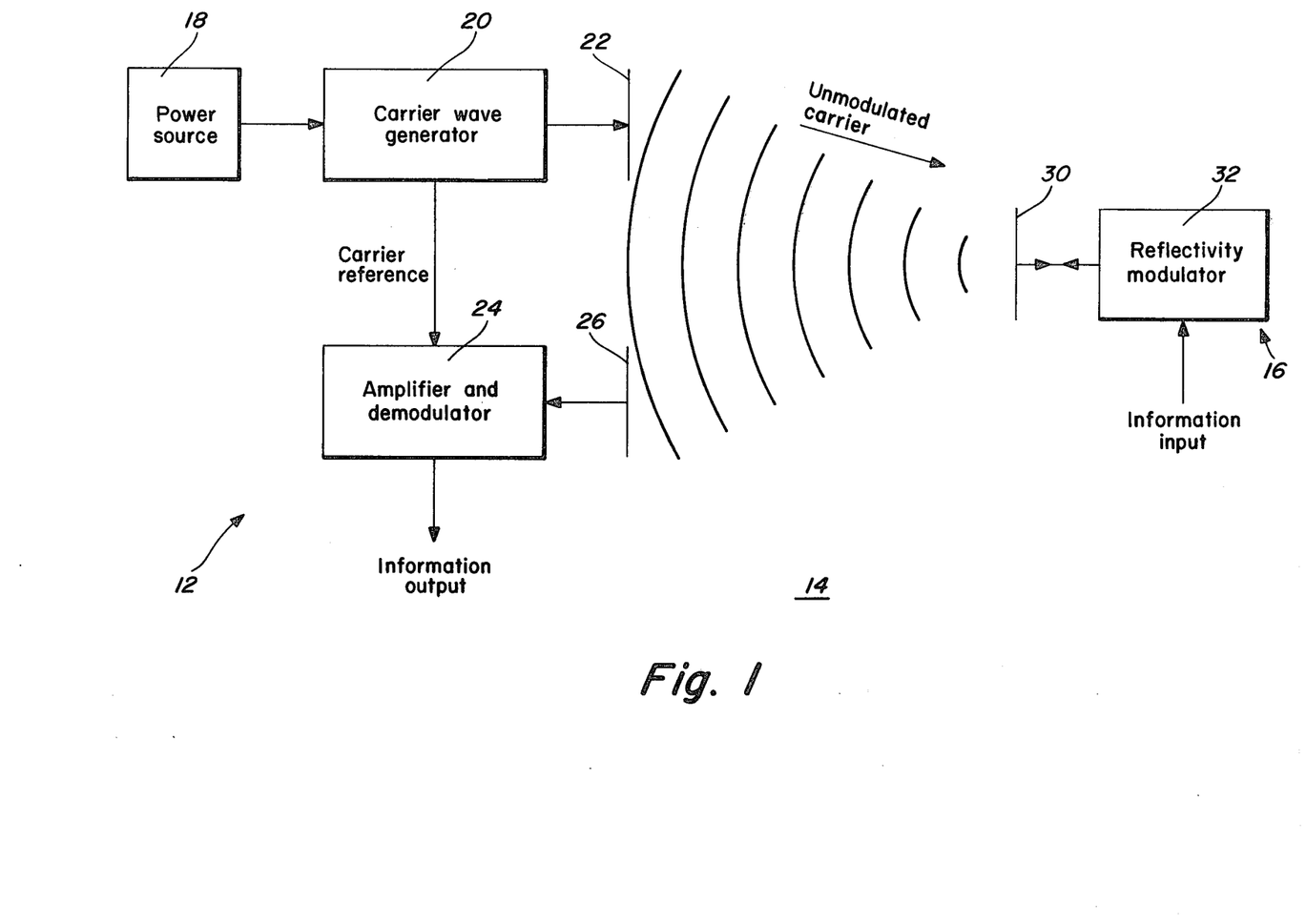
FIG. 1 illustrates a block diagram of the preferred embodiment of the invention.

Reference is now made to FIG. 1 which is a block diagram of the preferred embodiment of the invention. The system comprises an interrogator 12, a transmission medium 14 and a transponder 16. The signal generating and transmitting portion of the interrogator comprises a power source 18, a carrier wave generator 20 and a sending transducer or antenna 22. In addition, the interrogator also comprises an amplifier and demodulator 24 operably connected to a signal receiving transducer or antenna 26.

The transmission medium preferably comprises air, but a medium such as water or a solid could be utilized in combination with a signal appropriate for traveling therethrough.

The transponder 16 comprises a signal receiving and reflecting antenna 30 and a reflectivity modulator 32 for modulating the signal received by antenna 30 as well as for reflecting the modulated signal from antenna 30. Reflectivity modulator 32 can be disposed, for example, on the animal to be monitored. In the case of a steer which it is desired to monitor for temperature changes, it would be connected to an appropriate thermistor embedded in the animal. However, it will be appreciated by those skilled in the art that what particular information passes through the system of the invention is not part of the invention and the invention is not restricted to the use of the system disclosed herein in animal monitoring. Clearly, the invention may be used by those skilled in the art in many other monitoring environments and applications.

As can be seen from FIG. 1 the power source 18 powers the carrier wave generator 20 to send a generated signal from transducer or antenna 22. The signal from antenna 22 passes through transmission medium 14 and is received by a reflector 30 at the transponder 16. The reflectivity modulator 32 modulates such a signal in accordance with information desired and reflects the amplitude modulated signal from reflector 30 back on to the reflected signal receiving antenna 26. The signal impinging on antenna 26 is picked up by the amplifier and demodulator 24 which processes the signal and determines the information carried thereby.

As will be appreciated by those skilled in the art, power source 18 and carrier wave generator 20 are readily available pieces of equipment. Too, radio frequency transmitting and receiving antennas such as antennas 22, 26 and 30, are well known to those skilled in the art. Thus, no further discussion need be made of these components.

While the telemetry system shown in the block diagram of FIG. 1 is a preferred embodiment of this invention, typical of what might be used at radio frequencies, there are many variations that will be obvious to those familiar with radio frequency communication and telemetry techniques.

The carrier generated at the interrogator need not be continuous wave or constant in amplitude and/or frequency. It may be appropriate in some applications to generate the carrier intermittently. This might be done for various reasons such as to conserve power, to minimize interference with other users of the spectrum, or for other reasons. Similarly, there may be situations where it might be useful to modulate the carrier in a particular area of a plurality of various ways. For example, command signals or information could be sent to the transponder unit from the interrogator by appropriately modulating the carrier sent from the interrogator. Such modulation of the carrier could be done in such a way as to not interfer with the modulation superimposed on the reflected carrier signal at the transponder. The information added to the carrier at the transponder could be made distinguishable and separable from that sent to the transponder by, for example, using sufficiently separated modulation frequencies or by using a different form of modulation, such as for example pulse modulation generated at the transponder superimposed on a variable frequency amplitude modulation sent from the interrogator. There are many other possible combinations which will be readily recognizable to those familiar with the state of the art in communications, telemetry, and radio control.

Figure 2:
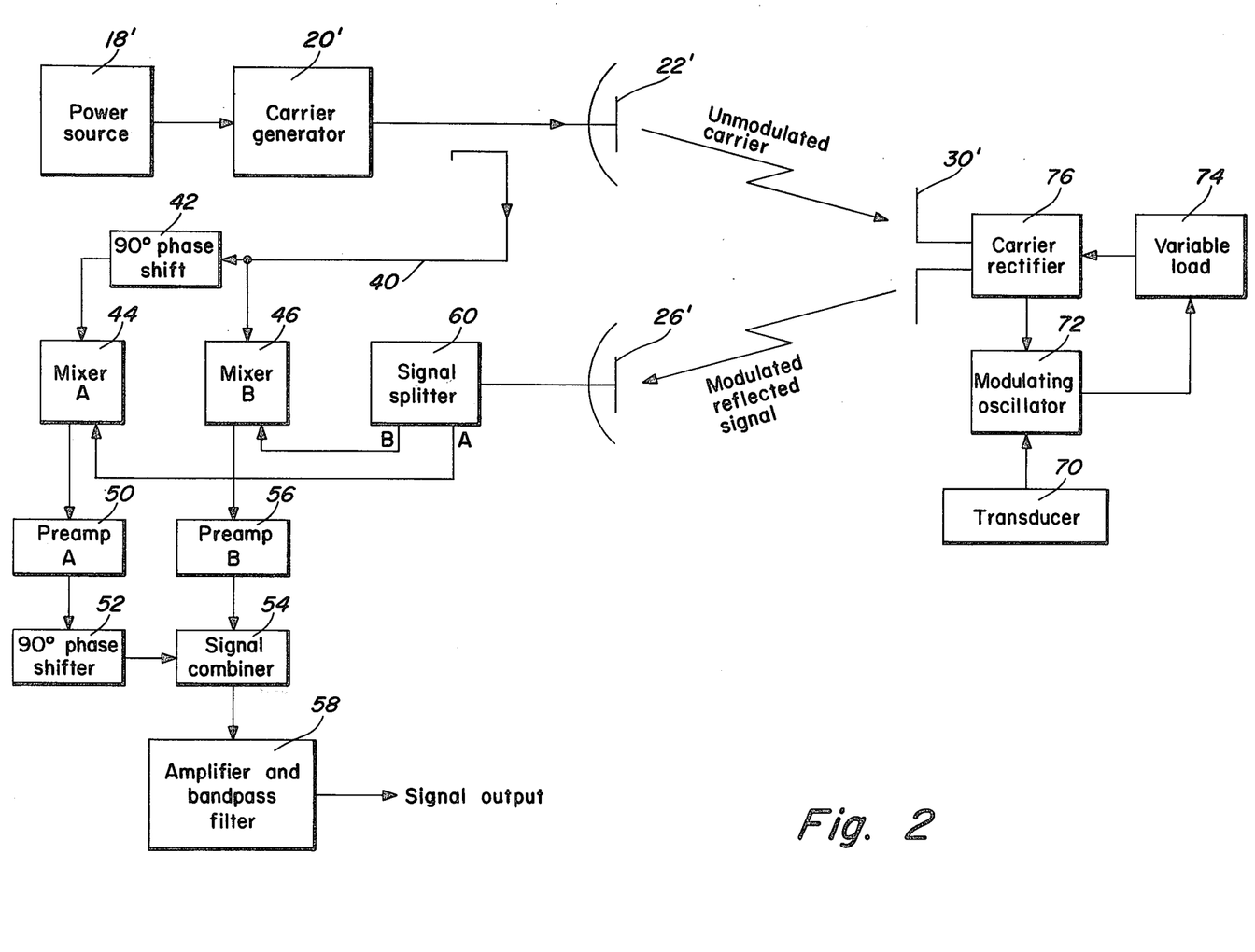
FIG. 2 shows a more detailed block diagram indicating the components of the blocks of FIG. 1.

FIG. 2 shows a more detailed block diagram of the preferred embodiment of the invention. As seen therein, power source 18' carrier wave generator 20', and antennas 22' 26' and 30' correspond to their unprimed numbers in FIG. 1. The amplifier and demodulator of FIG. 1 is broken down into its components in FIG. 2. The amplifier and demodulator comprises an attenuated carrier conduit 40, which passes a portion of the wave generated by generator 20' through a 90° phase shifter 42 to a mixer 44. Part of the generated wave goes directly to a mixer 46. From mixer 44, the phase shifted portion of the generated signal passes through a preamplifier 50 and 90° phase shifter 52 at the modulation frequency into a signal combiner 54. The signal from mixer 46 passes through a preamplifier 56 into signal combiner 54. The combined signals pass from signal combiner 54 into an amplifier and bandpass filter 58 to produce an output signal. The reflected signal received by antenna 26' passes into a signal splitter 60 which outputs into both mixer 44 and 46 where portions of the reflected signal are mixed with the portions of the generated signals.

While 90° phase shift devices are shown, any other combination of phase shifting means which will result in a net 90° phase difference between the local oscillator inputs to the mixers or a 90° phase difference between the receiver inputs to the mixers, or a combination of the two, will be suitable.

The transponder comprises a transducer 70, a modulation oscillator 72, a variable load 74 and a carrier rectifier 76 as well as antenna 30'.

In operation, power source 18' generates energy to power carrier wave generator 20'. Generator 20' produces a time variable signal, preferably a single frequency radio frequency signal. The rf signal is transmitted by carrier sending antenna 22' through the medium onto transponder antenna 30'. The received signal is rectified and modulated by oscillator 72 driven with transducer 70. The transponder can be a passive transponder, powered by energy from the signal receivedd by antenna 30'. It may also be active, powered by energy from its own separate source. In any case, transducer 70 causes modulation oscillator 72 to oscillate in accordance with the transduced parameter. The modulated oscillator signal passes through variable load 74 which amplitude modulates the signal. This modulated signal is reflected by carrier rectifier 76 through antenna 30'. Receiving antenna 26' receives the reflected modulated signal and passes it to signal splitter 60. Both the attenuated carrier signal from carrier wave generator 20' and the reflected modulated signal enter mixers 44 and 46. The mixers send their output through preamplifiers 50 and 56, and in the case of preamplifier 50, through a 90° phase shifter so that the signals entering combiner 54 are 90° or 270° out of phase and never 180° out of phase. The amplitude modulation in the reflected signal produced by the transponder shows up at the output of the signal combiner 54. It will be appreciated by those skilled in the art, that following or preceding the preamplifiers, any combination of phase-shifting devices which will result in a net quadrature phase relationship at the modulation frequency or band of frequencies between the two mixer output channels will be suitable. The output signal passes through an amplifier and a bandpass filter 58, to amplify the signal to an appropriate level and to eliminate noise. The resulting output represents the information transmitted from the transponder.

The output signal may be further processed as is appropriate for the particular application. For example, if the modulating frequency itself is the information, the output signal can be sent to a frequency counter to measure the frequency. If the information consists of amplitude, pulse, digital, phase, frequency or other modulation superimposed on the modulation frequency, appropriate means can be used to extract the information of interest.

It will be appreciated since no carrier signal is generated by the transponder there need be no large power source at that location to provide sufficient power to generate a carrier which would carry the information from the information sending terminal to the information receiving terminal, nor a means for determining the frequency of such a locally generated carrier.

A major advantage of the system of the invention is that the carrier frequency is available in pure unmodulated form in any location physically close to the information receiver. This provides for the use of coherent detection at the receiver. For example, in an rf system, a portion of the carrier signal from the carrier generator can be used as a local oscillator input to the receiver mixer as shown in FIG. 2. Alternatively, the local oscillator signal could be created by translating the carrier frequency in a small fixed or variable amount. The advantage of coherent detection is that system bandwidth can be reduced to that necessary for passing the information signal only, with a minimization of noise.

Naturally, reduced bandwidth enables better noise rejection. The use of coherent detection also eliminates the necessity for close control over carrier frequency, providing for the use of simpler and lower cost carrier generation devices than would otherwise be required.

It is possible to get response from one transponder to two interrogators or more, simultaneously and without interference. All that is required is sufficient difference in the carrier frequencies to put the frequency difference outside the modulation signal passband.

While only a single transponder antenna is shown in FIG. 2, two or more antennas may be suitably interconnected into an array so as to receive and reflect a larger amount of carrier power. Such an array can also be used to produce directivity for the transponder antenna. Alternatively, any of the known methods for making a directive antenna can be used at the transponder to augment the directivity and power gain of the transponder antenna.

Although FIG. 2 shows only a single transponder, two or more transponders may be used simultaneously. Information from a plurality of transponders can be received in one or more of a number of different ways. For example, the carrier from the interrogator can be beamed selectively to one or more of the transponders. In addition, different modulation frequencies can be used at the different transponders and the information separated at the receiver with appropriate bandpass filters. One can also arrange to have the transponders send information at different prearranged times. One could also superimpose a unique, prearranged identification code on the transponder return signal so that the transponder originating a signal could be recognized. Alternatively, a unique interrogation command or control signal for each transponder can be impressed as modulation on the carrier sent from the interrogator to commad response from a particular transponder.

The modulating signal fed to the variable load may be in the form of audio signals, pulses, digital signals, video signals and other signals that will be familiar to anyone conversant to the state of the art. The frequency of the modulating oscillator may be determined by the state of closure of a switch or an array of switches. In addition, a combination of modulations may be used, such as digital information superimposed on a modulation frequency determined by a physical parameter.

While the description of the system shown in FIG. 2 specifically shows amplitude modulation of the carrier signal reflected from the transponder unit, there are other ways to vary the reflectance characteristics at the transponder to produce a reflected carrier with superimposed information which can be extracted at the interrogator. For example, it is possible to vary the phase of the returned signal instead of its amplitude, or use a combination of the two methods. Phase modulation could be produced, for example, by varying a reactance placed across the transponder antenna. Alternatively, phase differences in the return signal can be generated by using two or more antennas appropriately different in distance from the interrogator antenna and amplitude modulating the reflectivity of each. If such phase modulation is used, then the means used at the interrogator receiver to make the receiver insensitive to the phase of the returned signal would not be used.

Figure 3:
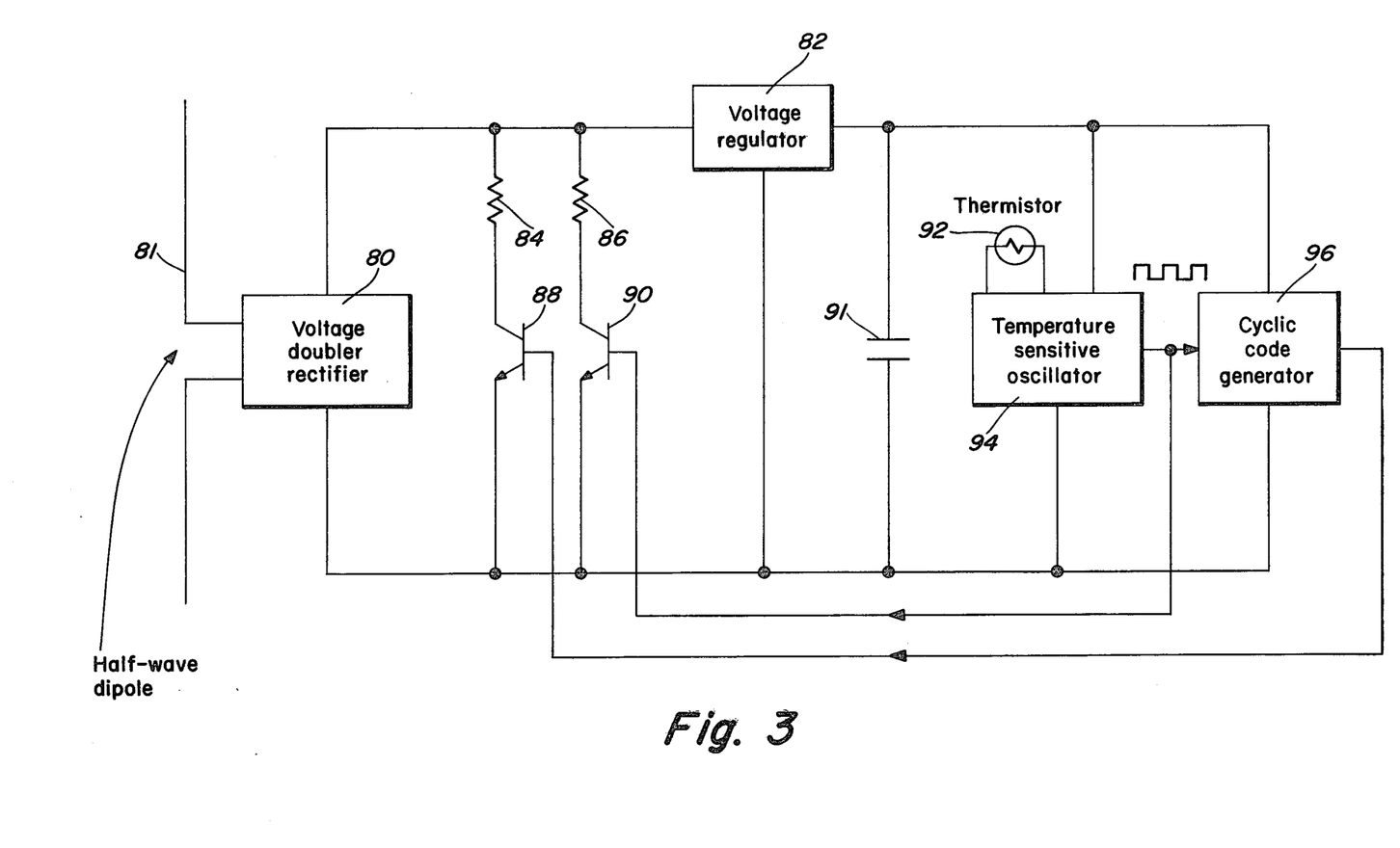
FIG. 3 shows a detailed schematic of a passive transponder in accordance with the invention.

FIG. 3 shows in block diagram form, the circuitry of a passive (rf beam-powered) transponder to convey both temperature and digital information. The temperature is sensed in analog form by a thermistor 92 connected to a temperature sensitive oscillator 94, which is made suitably temperature sensitive in its oscillation frequency by having the thermistor connected into one of the frequency determining resistances. Alternatively two or more thermistors could be used.

An rf signal received by a half-wave dipole antenna 81 is passed to a voltage doubler rectifier 80. A voltage doubler type of rectifier is used to give twice the dc output voltage as would be available from a simple half-wave rectifier. Any other type of rectifier can be used, but a voltage doubler is the preferable one.

In this circuit, the dc voltage from the rectifier 80 is used to power the transponder circuitry. Of course, the transponder circuitry could be powered from a different power source such as in the aforementioned active transponder embodiment. When the rectified rf is used to power the circuitry, a voltage regulator 82 is interposed between the rectifier output and the circuitry to be powered. This ensures that a suitably regulated voltage is available for the circuitry. An energy storage capacitor 91 is used following the voltage regulator. The purpose of this is to store operating energy for the circuitry to provide operation during the low rectifier output voltage periods that will be generated in the amplitude modulation process.

Transistor 90 is used as a swich, driven by the output of the temperature sensitive oscillator 94, and alternately, in effect, placing resistor 86 across the output terminals of the rectifier. Resistor 86 is selected to be of such resistance that it will partially modulate the reflectance of the antenna and, with only transistor 90 and resistor 86 in operation, the antenna reflectance will be modulated in accordance with the frequency of the temperature sensitive oscillator 94. Because the modulation frequency is dependent upon the temperature sensed by the thermistor 92, the reflected rf is therefore amplitude modulated at a frequency dependent upon the temperature.

In the use of the transponder to send a fixed digital code for identification means, the depth of modulation produced by the temperature sensitive oscillator is varied in accordance with a lower frequency digital signal which comprises a suitable unique code corresponding to the identity of a particular transponder. In the preferred embodiment, the rate of this identification signal is made an integral fraction of the rate of the oscillator, but this need not be so.

In the circuit shown, the depth of modulation is varied in accordance with the digital code by means of transistors 88 and 90. Transistor 90 is driven by the oscillator. Transistor 88 is driven by the cyclic code generator, which produces the identification code. In the preferred circuit the code is generated repeatedly as long as the circuit is powered, but this is not necessary. Transistors 88 and 90 comprise a logical AND circuit and this is one means for performing that logical function. When both transistors 88 and 90 are turned on, a resistor 84 is effectively disposed across the output terminals of rectifier 80.

It will be apparent that when both resistors 84 and 86 are placed across the rectifier terminals, rectifier 80 is more heavily loaded than when only resistor 86 is placed across the rectifier. Therefore, more energy is extracted from the rectifier.

Figure 4:
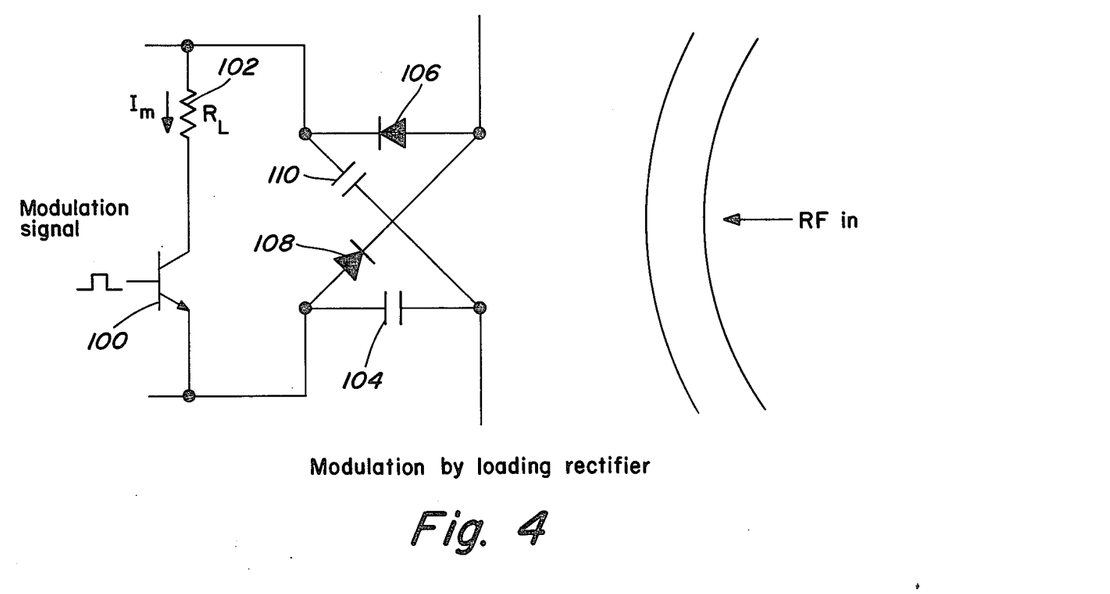
FIG. 4 shows a loading rectifier modulator for the transponder in FIG. 3.
Figure 5:
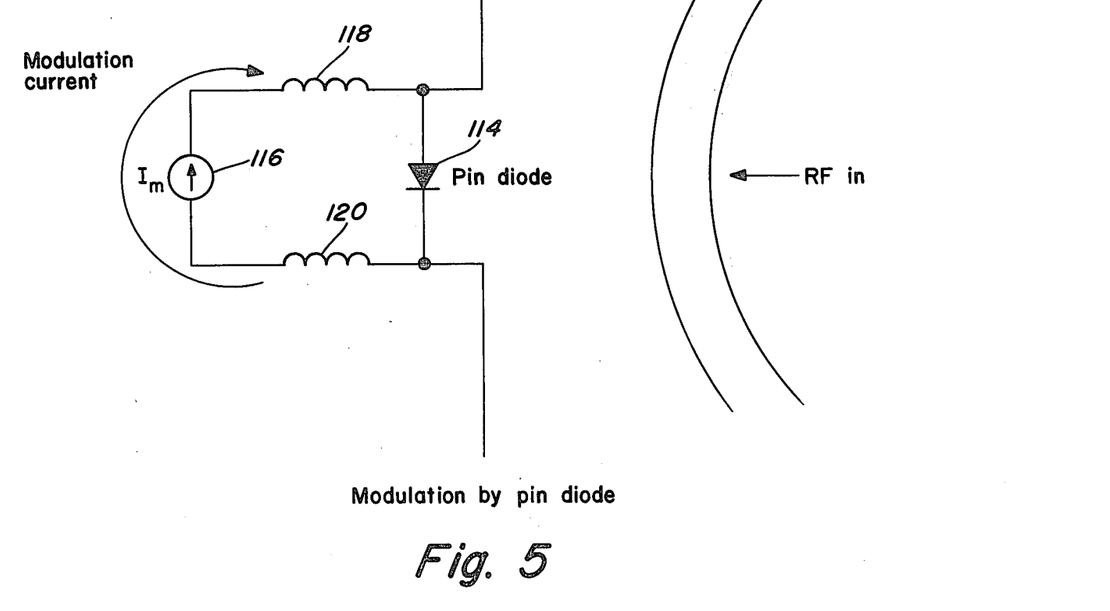
FIG. 5 shows a PIN diode modulator for the transponder of FIG. 3.

Modulation of the return signal by loading the transponder antenna is shown in FIGS. 4 and 5. FIG. 4 shows modulation by a loading rectifier whereas FIG. 5 illustrates modulation by PIN diode. The rf current flowing in the antenna is a function of the dc load on the rectifier output. The heavier the dc load, the greater the rf current flowing from the antenna into the rectifier input. The rf reflected or scattered from the antenna is proportional to the rf current flowing in the antenna. Since this rf current is a function of the dc load on the rectifier, the reflected rf from the antenna is also a function of the dc load on the rectifier.

In accordance with the invention, rf reflected from the transponder antenna can be modulated by any means that alters the rf current flowing in the antenna. Any means that can be used to alter the resistance, or reactance across the antenna terminals in accordance with a desired modulation pattern can be used. FIG. 4 shows a voltage doubler rectifier, but any other rectifier arrangement could be used.

The rf current flowing into the rectifier from the antenna is a function of the dc current extracted from the rectifier. The higher the dc load on the output, the higher the rf current flowing from the antenna. One means of varying the load current from the rectifier output is to vary the value of a resistance placed across the rectifier output. In FIG. 4, resistor 102 is switched in and out of the circuit by a transistor 100.

A rectifier comprising diodes 106 and 108 and capacitors 104 and 110 is a preferred means of modulation for a passive transponder since the dc output from the rectifier can be used to supply power to the transponder circuitry.

As shown in FIG. 5, another means for varying the rf current in the antenna and thereby modulating the rf signal reflected from it, is to use a PIN 114 diode as a variable rf resistance. The rf resistance of PIN diode 114 is controlled by varying a low frequency or dc current 116 passing through the diode. A suitable pair of inductors 116 and 118 or other suitable means that present a high impedance to rf and a low impedance to the modulation current can be used to isolate the modulation circuitry from the antenna.

Figure 6:
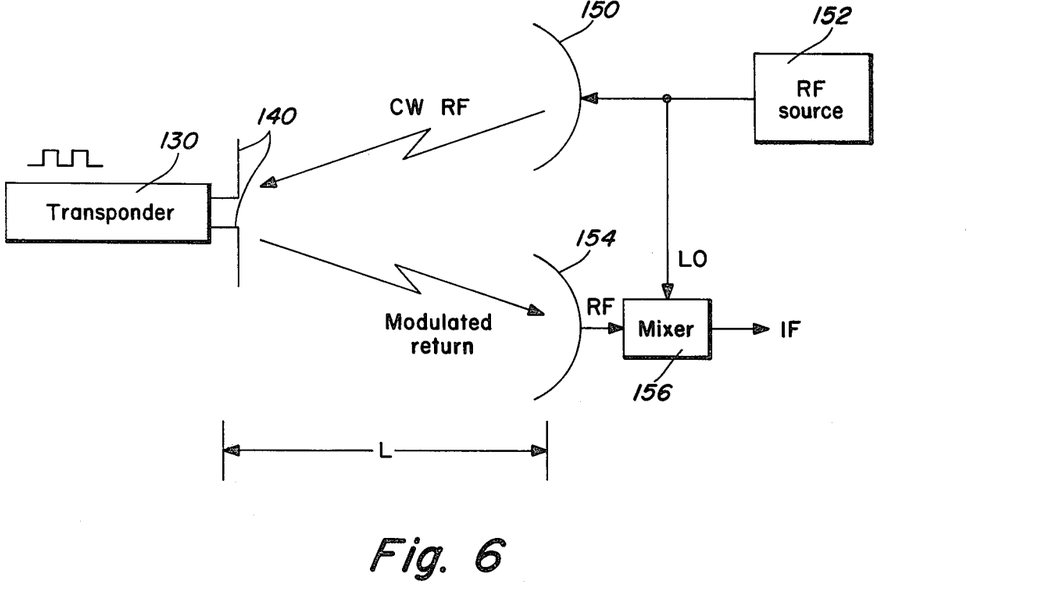
FIG. 6 illustrates a telemetry system utilizing only one mixer.

FIG. 6 shows a system utilizing a single antenna for both transmitting an rf carrier from the rf generator and receiving the reflected signal and passing it to the receiver mixer while blocking the much larger transmitted carrier signal.

A 3-port circulator is used. This is a device commonly used in microwave rf systems for similar isolation applications. The three ports are labeled A, R, and T to indicate respectively antenna, receiver, and transmitter. The circulator device has the property that rf energy is passed with little attenuation from one port to the next in the clockwise direction as shown in FIG. 6. For example, the transmitter signal is passed with little loss from port T to port A and from there to the antenna. Similarly, the signal received at the antenna is passed easily from port A to port R and from there to the receiver mixers. Signal transmission in the other direction, which is not desired, is almost completely blocked by the action of the circulator. Reverse signal transmission is typically a factor of 20 to 30 dB lower than forward signal transmission. This is called the directivity of the circulator.

In the circuit of FIG. 6, the circulator is used to allow operation from a single antenna. The rf carrier from the rf source is preferentially passed to the antenna and is blocked from passing to the receiver input, where it is not wanted. Similarly, the reflected rf signal picked up at the antenna is preferentially passed to the receiver input and is blocked from passing back to the rf source, where it would be wasted.

Since the circulator only has a finite amount of directivity, however, it is usually the case that the small amount of reverse transmission in the circulator from port T to port R would result in more rf carrier being sent to the receiver input than is desired. One consequence of this could be to destroy the receiver mixers and another could be to cause the mixers to malfunction. A means to overcome this difficulty is to arrange to feed into port A of the circulator some rf signal of the proper amplitude and phase to pass through the circulator from port A to port R to just cancel the reverse transmitted "leakage" from port T. One way of implementing this is to interpose a suitable rf tuning device between port A and the antenna. A double stub tuner is such a suitable device. The tuner has the additional function of matching the antenna impedance for maximum efficiency in both transmitting and receiving the rf signals.

FIG. 6 shows the path of the rf signals in simplified form. The rf carrier is sent from an antenna 150 from an rf source 152. The carrier passes through a transmission medium to an antenna 140 on a transponder 130, from which a modulated signal is reflected back to a receiving antenna 154. A separate receiving antenna is shown for simplicity in description, though in practice suitable means are available for using a single antenna. The received signal is passed to a mixer 156, where it is mixed with an attenuated unmodulated signal from the rf source fed into the LO or "local oscillator" port.

The output from the mixer 156, usually designated the IF or "intermediate frequency" output in ordinary receiver practice, is a replica of the signal used to modulate the rf signal at the transponder and therefore contains the information put on the rf signal at the transponder. However, the amplitude and phase of this modulation signal are affected by the relative rf phase of the rf and LO inputs to the mixer. The relative phase of these signals is determined by the distance that the rf signal traverses in going from the transmitting antenna to the transponder and back to the receiving antenna, including also the distances in the connection from the antennas to the mixer. As this distance varies, the relative phase of the rf inputs to the mixer vary. One particular disadvantage of this is that if the rf and LO inputs happen to be quadrature phase, the mixer output will be zero, i.e., the output will pass through a "null." This is particularly disadvantageous when the transponder is in motion relative to the transmitter/receiver antenna unit and vice versa since the receiver signal may drop out, causing some information to become lost.

This undesired effect has been called the "interferometer" effect since the principle causing it is similar to that of an interferometer.

Figure 7:
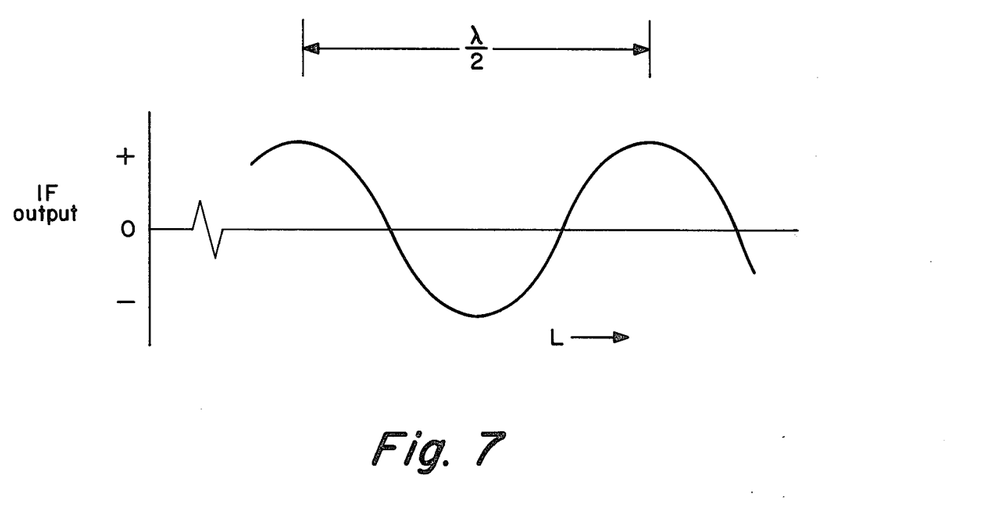
FIG. 7 shows the interferometer effect with a single mixer; such as in the system of FIG. 6.

FIG. 7 shows how the amplitude and phase of the mixer output are a function of the distance between the transponder and the transmitter/receiving antenna unit. It will be seen that the relationship is sinusoidal with distance, being cyclic with a half wavelength at the rf carrier frequency used and dropping to zero in amplitude every quarter wavelength.

Figure 8:
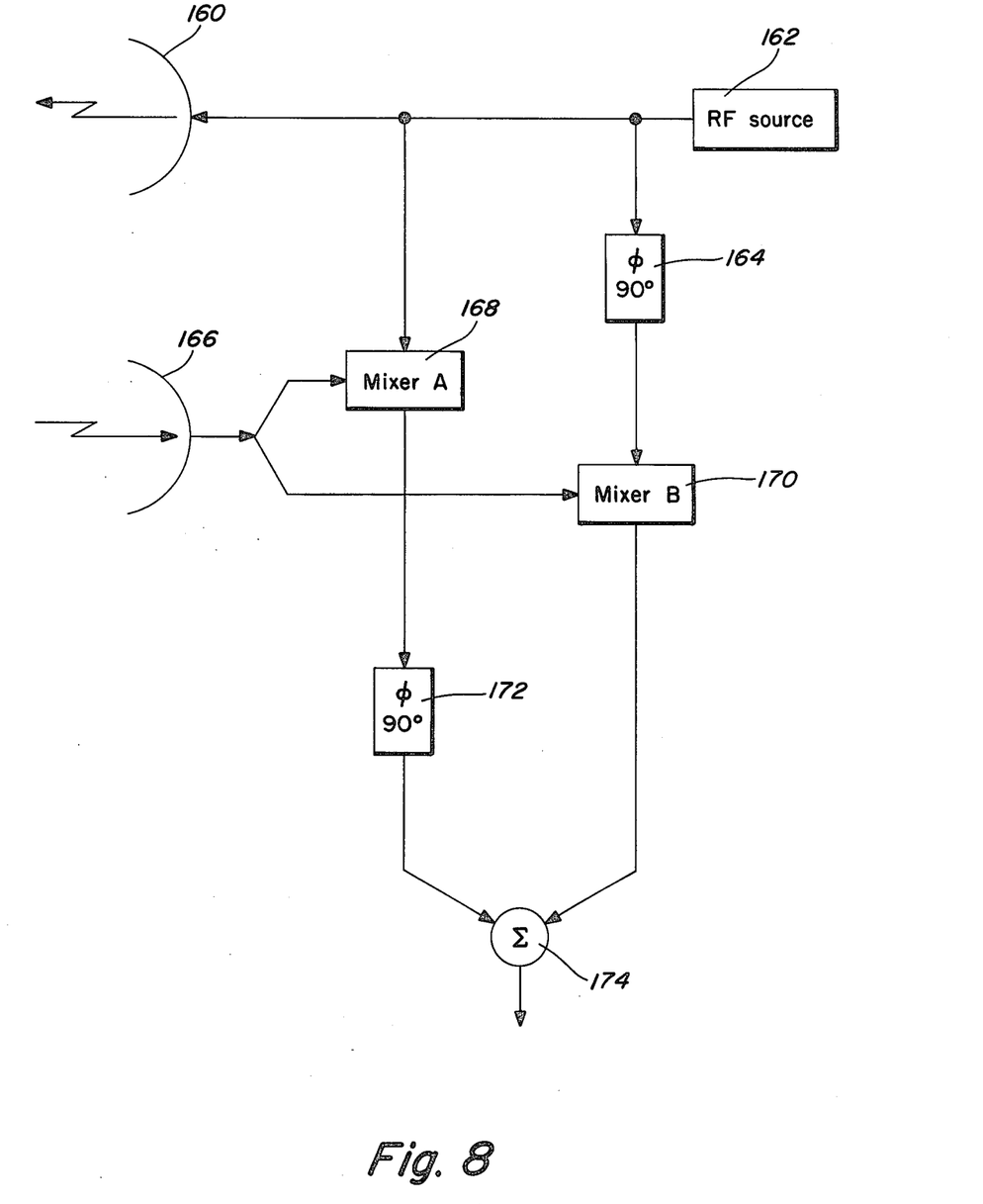
FIG. 8 shows apparatus utilized in accordance with the invention for removing the interferometer effect of the FIG. 6 apparatus.

FIG. 8 shows a system for removing the interferometer effect of FIGS. 6 and 7 and for making signal reception from the transponder independent of the distance between antennas 160 and 166.

A single rf source 162 is utilized. Two rf mixers 168 and 170 are used instead of only the single one common in most receiver systems. A phase shifting 164 ensures that there is a relative 90° difference in the phases between the rf and LO inputs to the two mixers. Alternatively, this phase shift could be introduced in the rf input of one of the mixers, or split up in one of a number of different ways to get the net 90° difference. Thus, if the phase relationships are such that one of the mixer outputs is at a null point, the other output is at a maximum, and vice versa. It will be appreciated that it is impossible for both mixer outputs to be at a null at the same time. Therefore there will always be a mixer output from which the modulation signal can be obtained.

While mixer output signals cannot be zero or null at the same time, their amplitude will vary with the rf phase or antenna spacing and their outputs may be in phase or out of phase at the modulation frequency. This makes it difficult to utilize the mixer outputs directly to recover the modulation signal.

FIG. 9 illustrates a system avoiding this difficulty. A relative 90° phase shift at the modulation frequency is produced between the two mixer outputs by phase shifter 172. The phase shifted signals are linearly combined by summing amplifier 174 to produce a single output at the modulation frequency. Of course, any method that produces a net 90° phase shift between the mixer output signals should function as well as phase shifter 172.

The effect of combining the mixer output signals is to make the combined signal amplitude independent of the rf signal phase and therefore of the antenna spacing. Qualitatively, it is easy to see that if the mixer output signals at the modulation frequency are phase shifted to be in quadrature phase with respect to each other, they cannot cancel each other out to zero in the linear combining operation, and therefore there will always be some combined output signal at the modulation frequency. A more careful analysis will show that the amplitude is actually constant.

The various features and advantages of the invention are thought to be clear from the foregoing description. However, various other features and advantages not specifically enumerated will undoubtedly occur to those versed in the art, as likewise will many variations and modifications of the preferred embodiment illustrated, all of which may be achieved without departing from the spirit and scope of the invention as defined by the following claims.

We claim:

1. In telemetry apparatus, a passive transponder comprising:
   an antenna;
   rectifier means having a first pair of terminals connected to said antenna and having a second pair of terminals providing direct current;
   variable loading means connected to said second pair of terminals; and
   information encoding means in circuit with said variable loading means to enable encoded information to vary the direct current drawn from said rectifier by said variable loading means, thereby varying the impedance of said rectifier means at said first pair of terminals, and varying the reflectivity of said antenna.

2. In the transponder set forth in claim 1, said variable loading means including a resistor in circuit with semiconductor switching means responsive to said information encoding means and connected to said rectifier means.

3. In the transponder set forth in claim 2, said information encoding means including a condition sensitive variable frequency oscillator.

4. In the transponder set forth in claim 3, a voltage regulator connected in circuit between said variable loading means and said variable frequency oscillator.

5. In the transponder set forth in claim 1, said rectifier means including current storage capacitor means.

6. In the transponder set forth in claim 5, said rectifier means and said current storage capacitor means forming a voltage doubler rectifier circuit.

7. In the transponder set forth in claim 6, said rectifier means including:
   a first diode connected between one of said first pair of terminals and the adjacent one of said second pair of terminals;
   a second diode connected to said first diode at one of said first pair of terminals and the opposite one of said second pair of terminals;
   a first current storage capacitor connected between the other said first pair of terminals and the adjacent one of said second pair of terminals; and
   a second current storage capacitor connected to said first diode at said first pair of terminals and to said first current storage capacitor at said first pair of terminals.

8. In the transponder set forth in claim 3, said information encoding means further including cyclic code generator means connected to said variable frequency oscillator.

9. In the transponder set forth in claim 8, second variable loading means connected to said cyclic code generator.

10. A passive transponder adapted to be implanted beneath the skin of a living animal, comprising:

an antenna;
a voltage doubling rectifier having first and second terminals connected to said antenna, and having third and fourth terminals;
an audio frequency oscillator;
a temperature sensitive resistor connected to said audio oscillator to vary the frequency of said audio oscillator in response to ambient temperature changes;
variable rectifier loading means including a resistor connected to said third terminal, a transistor having a collector connected to said resistor, an emitter connected to said fourth terminal, and a base electrode connected to said audio frequency oscillator.

* * * * *